United States Patent [19]
Horikoshi et al.

[11] 4,348,384
[45] Sep. 7, 1982

[54] PHARMACEUTICAL COMPOSITION FOR ORAL ADMINISTRATION CONTAINING COAGULATION FACTOR VIII OR IX

[75] Inventors: Isamu Horikoshi; Nobuo Sakuragawa; Masaharu Ueno; Kaoru Takahashi, all of Toyama, Japan

[73] Assignee: Dainippon Pharmaceutical Co., Ltd., Osaka, Japan

[21] Appl. No.: 309,269

[22] Filed: Oct. 7, 1981

[30] Foreign Application Priority Data

Oct. 17, 1980 [JP] Japan .............................. 55/144508
Apr. 28, 1981 [JP] Japan .............................. 56/65685

[51] Int. Cl.³ ............................................. A61K 35/14
[52] U.S. Cl. .................................. 424/101; 424/177; 424/199; 424/365
[58] Field of Search ............... 424/101, 365, 199, 177

[56] References Cited

U.S. PATENT DOCUMENTS 4,183,960  1/1980  Asher et al. ..................... 424/365

*Primary Examiner*—Sam Rosen
*Attorney, Agent, or Firm*—Wegner & Bretschneider

[57] ABSTRACT

A pharmaceutical composition suitable for the treatment and prophylaxis of hemophilia A or B, which comprises coagulation factor VIII or IX and a protease inhibitor (particularly aprotinin) which are incorporated in liposomes and optionally lyophilized and/or encapsulated in intestine capsules. The composition can give high absorption of the required coagulation factor from intestinal tract without being decomposed in gastrointestinal tract even by administration in oral route.

14 Claims, No Drawings

PHARMACEUTICAL COMPOSITION FOR ORAL ADMINISTRATION CONTAINING COAGULATION FACTOR VIII OR IX

The present invention relates to a pharmaceutical composition for oral administration containing coagulation factor VIII or IX. More particularly, it relates to a novel pharmaceutical composition suitable for the treatment or prophylaxis of hemophilia A or B by oral administration, which comprises coagulation factor VIII or IX and a protease inhibitor which are incorporated in liposomes and optionally lyophilized and/or encapsulated in intestine capsules.

It is well known that hemophilia is one of the hereditary coagulation disorders due to bleeding factors, and the existent hemophiliac appears one per 22 thousand persons in men and such a disorder may appear in a ratio of one per about 8,000 birth population in men. Among these coagulation disorders, hemophilia A is due to hereditary deficiency of coagulation factor VIII and hemophilia B is due to hereditary deficiency of coagulation factor IX. Such disorders may be substantially remedied by supplement of the coagulation factors to patients who are deficient in such factors.

The supplement of the required coagulation factors had been done by infusion of fresh blood, but recently, with development of preparation containing the factors in high concentration, there have widely been used concentrated preparations containing much amounts of the coagulation factors and less amount of other factors such as fibrinogen.

However, these preparations are usually administered intravenously, and hence, it is required to develop a preparation for oral administration which is more easily handled than the injection preparations.

When the coagulation factors VIII and IX are merely incorporated into the conventional oral preparations such as aqueous preparation, tablet, or capsule, they are decomposed by hydrochloric acid or pepsin in stomach or with enzymes such as trypsin or chymotrypsin in intestinal or pancreatic juice, and hence, they can not effectively be absorbed from intestinal tract with keeping their activity.

The oral administration of coagulation factor VIII was firstly reported by Hemker et al, wherein the factor VIII was treated with liposomes [cf. H. C. Hemker et al., Lancet, 8159, 70 (1980) and PCT International Publication No. WO80/01456]. The present inventors re-examined the Hemker's method, but they could not obtain satisfactory results. This means that even if the coagulation factor VIII is enclosed in liposomes, it is easily decomposed by various enzymes contained in gastric juice or intestinal juice when administered orally, and hence, it can not be absorbed from intestinal tract with keeping its activity. With respect to the coagulation factor IX, there is no report that the factor IX is orally administered after being treated with liposomes.

Thus, there has never been known any oral preparation of coagulation factor VIII or IX which can be administered orally and the factors can effectively be absorbed from intestinal tract without being decomposed in gastrointestinal tract.

As a result of the present inventors' intensive study, it has been found that an improved oral preparation of coagulation factor VIII or IX can be obtained by incorporating the factors in liposomes together with a protease inhibitor, optionally followed by lyophilization and/or encapsulating in intestine capsules.

An object of the present invention is to provide an improved pharmaceutical composition of coagulation factor VIII or IX for oral administration, which is useful for oral treatment and prophilaxis of hemophilia A or B. Another object of the invention is to provide a novel pharmaceutical composition of coagulation factor VIII or IX which is effective for absorption of the factors from intestinal tract without being decomposed in gastrointestinal tract. These and other objects and advantages of the present invention will be apparent to persons skilled in the art from the following description.

The pharmaceutical composition of the present invention comprises coagulation factor VIII or IX and a protease inhibitor which are incorporated in liposomes. The composition is preferably encapsulated in intestine capsules in order to be less affected with gastric juice and duodenal juice. Moreover, the composition is preferably lyophilized in order to increase storage stability. In another embodiment, the coagulation factor VIII or IX, the protease inhibitor and the material for forming liposomes are each lyophilized, and the lyophilized materials are mixed and then encapsulated in intestine capsules. The pharmaceutical composition of the present invention may optionally be incorporated with stabilizers such as mannitol, albumin, dextran, etc, and further with other additives for improving the fluidity of the lyophilized product such as glucose, lactose, mannitol, etc.

The coagulation factors VIII and IX are originated from human and other mammals such as pigs and bovines.

The protease inhibitor used in the present invention includes aprotinin, dimethylcarbamoylmethyl p-(p-guanidinobenzoyloxy)phenylacetate.mesylate, etc. The protease inhibitor is preferably incorporated in an amount of 10 to 100 units per 1 unit of the coagulation factor VIII or IX.

For absorbing effectively the coagulation factor VIII or IX into the absorption cells, the liposomes have preferably a size of about $1\mu$ and are preferably formed into multilamellas such as 2 to 3 lamellas. Besides, the aqueous phase enclosed in the liposomes has an osmotic pressure higher than that of absorption cells. The material for forming liposomes include all conventional materials. Preferable example of the materials is a phospholipid comprising predominantly yolk lecithin, wherein an appropriate amount of phosphatidic acid or phosphatidylserine is added in order to improve the liposome-forming ability or stability of the liposomes. Besides, cholesterol may also be incorporated in order to strengthen the liposome membrane, and further lysolecithin may be added in order to promote the fusion of the liposome membrane with the biomembrane of absorption cells. Phosphatidic acid is effective for enlarging the particles of liposomes, which results in increase of the amount of the materials enclosed therein. Phosphatidylserine is effective for improving the membrane forming ability.

When phosphatidic acid is added during enclosing coagulation factor IX in the liposomes, $Ca^{++}$ ion is preferably added in order to increase the uptake of factor IX into the liposomes. The uptake of factor IX is also increased by adding stearylamine to yolk lecithin.

The liposomes used in the present invention should have the following properties.

(i) Even if the liposome phase is separated by centrifuge and the outer phase has only a few water content, the liposome can keep its basic shape.

(ii) When the liposomes obtained by centrifuge as in the above item (i) are lyophilized, the lyophilized product can easily be restored to the original liposome state by adding water to the product.

(iii) When coagulation factor VIII or IX, protease inhibitor and material for forming liposomes are lyophilized, the mixture of these lyophilized materials can easily form the desired liposomes by adding water to the mixture.

The coagulation factor VIII or IX and protease inhibitor can be enclosed in liposomes by a conventional method as disclosed in a literature, e.g. "Methods in Cell Biology," edited by David M. Prescott, Vol. XIV, page 34. In order to prevent undesirable lowering of the activity of coagulation factors during the enclosure into liposomes, it is preferable to use a neutral buffer solution.

When the pharmaceutical composition of the present invention, wherein coagulation factor VIII or IX and a protease inhibitor are enclosed in liposomes, is administered orally, it reaches to and is absorbed at the absorption area (epithelial cells) in small intestine without decomposition of the factor VIII or IX even by being contacted with digestive juice in gastrointestinal tract. When the composition is encapsulated in intestine capsule, it reaches to small intestine by passing through stomach and duodenal tract as it stands, and the capsule is degradated in the small intestine at neutral or alkaline pH to release the contents thereof into intestinal tract. Because of coexistence of a protease inhibitor, the factor VIII or IX is protected from decomposition in small intestine and is effectively absorbed.

Thus, the pharmaceutical composition of the present invention is useful for oral treatment and prophylaxis of hemophilia.

The dose of the pharmaceutical composition of the present invention may be variable in accordance with the age, body weight, sex of the patients and also severity of symptom, but it is usually used in such an amount that the active ingredient is administered in the range of 500 to 3,000 units per day in case of coagulation factor VIII and in the range of 200 to 2,000 units per day in case of coagulation factor IX.

The excellent therapeutic effects of the pharmaceutical composition of the present invention were confirmed by the following clinical and animal tests.

TEST 1

To a female patient suffered from hemophilia A was administered coagulation factor VIII in the following preparations on different days.

Oral administration (1) The composition (20 intestine capsules) obtained in Example 4 was orally administered.

(2) The composition (50 ml) obtained in Reference Example 1 was orally administered.

Intravenous injection

A commercially available injection preparation of coagulation factor VIII: Concoeight ® (made and sold by Green Cross Co. in Japan) was intravenously administered in 250 units.

Before and after the administration of the preparations, blood was taken out at a fixed interval, and the activity of factor VIII in blood was assayed by the one stage method by Matsuoka (cf. Matsuoka, M; "Laboratory methds of blood coagulation," Kanahara, pages 61–165, Tokyo, 1977), wherein the amount of coagulation factor VIII is shown by percentage (%) when it is calculated in such a way that the amount of coagulation factor VIII in normal person is 100% and that of person having no coagulation factor VIII is 0%. The results are shown in Table 1.

TABLE 1

| Preparations | Route | Time of taking out blood (hour) | | | | | |
|---|---|---|---|---|---|---|---|
| | | 0 | 2 | 4 | 6 | 8 | 10 |
| Composition of Example 4 | p.o. | 2.0 | 3.4 | 3.3 | 3.3 | — | — |
| Composition of Ref. Ex. 1 | p.o. | 2.0 | 1.8 | 2.0 | 1.9 | 1.7 | — |
| Injection preparation | i.v. | 2.0 | 11.0 | 3.0 | 2.0 | 2.0 | 2.0 |

As is clear from the above results, when coagulation factor VIII was merely enclosed in liposome, the factor VIII was not effectively absorbed from intestinal tract with keeping its activity, but when it was enclosed in liposome together with aprotinin (protease inhibitor), it was absorbed well from intestinal tract with keeping its activity.

TEST 2

To a male patient suffering from hemophilia A was administered coagulation factor VIII in the following preparations on different days.

(1) The composition (20 intestine capsules) obtained in Example 4 was orally administered.

(2) The composition (20 intestine capsules) obtained in Reference Example 3 was orally administered.

Before and after the administration of the preparations, blood was taken out at a fixed interval, and the activity of factor VIII in blood was assayed in the same manner as in Test 1. The results are shown in Table 2.

TABLE 2

| Preparations | Time of taking out blood (hour) | | | | |
|---|---|---|---|---|---|
| | 0 | 2 | 4 | 6 | 8 |
| Composition of Example 4 | 1.4 | 1.8 | 2.1 | 1.8 | 1.9 |
| Composition of Ref. Ex. 3 | 1.4 | 1.3 | 1.3 | 1.4 | 1.3 |

As is clear from the above results, the factor VIII preparation incorporated with aprotinin could be absorbed well from intestinal tract with keeping its activity, but on the other hand, the factor VIII preparation containing no aprotinin could not be absorbed from intestinal tract with keeping its activity.

TEST 3

To a young male patient suffered from hemophilia A was administered coagulation factor VIII in the following preparations on different days.

(1) The composition (20 intestine capsules) obtained in Example 4 was orally administered.

(2) The composition (20 gelatine capsules) obtained in Reference Example 2 was orally administered.

Before and after the administration of the preparations, blood was taken out at a fixed interval, and the activity of factor VIII was assayed in the same manner as in Test 1. The results are shown in Table 3.

TABLE 3

| Preparations | Time of taking out blood (hour) | | | |
|---|---|---|---|---|
| | 0 | 2 | 4 | 6 |
| Composition of Example 4 | 2.0 | 2.8 | 2.8 | 3.5 |
| Composition of Ref. Ex. 2 | 2.0 | 1.9 | 1.9 | 2.0 |

As is clear from the above results, the factor VIII preparation incorporated with aprotinin could be absorbed well from intestinal tract with keeping its activity, but the factor VIII preparation containing no aprotinin could not be absorbed from intestinal tract with keeping its activity.

TEST 4

To a female Beagle dog, weighing 9.2 kg, was orally administered a suspension of the factor IX composition (10 ml) obtained in Examples 8 in a cow milk (200 ml). Before and after the administration of the preparation, blood was taken out and the activity of factor IX in blood was assayed by the one stage method by Matsuoka (cf. Matsuoka, M; "Laboratory methods of blood coagulation," Kanahara, pages 61-165, Tokyo, 1977), wherein the amount of coagulation factor IX is shown by percentage (%) when it is calculated in such a way that the amount of coagulation factor IX in normal Beagle dog is 100% and that of dog having no coagulation factor IX is 0%. The results are shown in Table 4.

TABLE 4

| Preparation | Time of taking out blood (hour) | | | | | |
|---|---|---|---|---|---|---|
| | 0 | 2 | 4 | 6 | 8 | 24 |
| Composition of Example 8 | 100 | 125 | 105 | 96 | 97 | 104 |

As is clear from the above results, the coagulation factor IX was absorbed well by the oral administration of the present pharmaceutical composition.

The preparation of the pharmaceutical composition of the present invention is illustrated by the following Examples but is not limited thereto.

EXAMPLE 1

Yolk lecithin (2 g) containing 5% of phosphatidic acid is dissolved in ethanol (40 ml). The solution is entered in a one-liter flask and is concentrated under reduced pressure, by which lecithin is deposited as a thin layer on the inner wall of the flask. After drying under reduced pressure, a phosphate buffer solution (pH 7.0, 50 ml) containing coagulation factor VIII (3,000 units) and aprotinin (150 thousand units) is added thereto, and the flask is lightly shaken to obtain a suspension of liposomes. The suspension of liposomes thus obtained is entered into a centrifugal tube and cooled to 10° C. and then centrifuged at 27,000 G for 20 minutes, by which creamy liposomes are obtained at the upper part. The transparent aqueous layer is again treated with lecithin and the mixture is treated in the flask in the same manner as above. The procedure is repeated three times. The creamy liposomes obtained in the above three times procedures are combined and suspended in physiological saline (50 ml), by which the outer layer of liposomes is washed. After cooling at 10° C., the suspension is centrifuged at 40,000 G for 10 minutes to collect liposomes, and the liposomes are dried in order to remove water contained in the outer layer thereof as largely as possible. The liposomes thus obtained have a volume of about 10 ml and contain coagulation factor VIII of 1,000 units and aprotinin of 50,000 units.

The liposomes obtained above are packed in gelatine capsules (size: #0, inner wall being coated with a thin layer of edible oil), which are further packed in intestine capsules so as to become double capsule structure. The joint of the outer capsules is completely sealed by treating them with a solution of the intestine capsule-forming material in acetone. The capsules contain coagulation factor VIII of 50 units per each capsule. When the capsules are kept at a cool and dark place, activity of the factor VIII does not lower within a short period of time.

EXAMPLE 2

In the same manner as described in Example 1, yolk lecithin (2 g) containing 10% of phosphatidic acid is dissolved in ethanol (40 ml) and the solution is concentrated under reduced pressure in a one-liter flask to deposit the lecithin as a thin layer on the inner wall of the flask. After drying under reduced pressure, a phosphate buffer solution (pH 7.0, 50 ml) containing coagulation factor VIII (3,000 units) and aprotinin (150 thousand units) is added thereto, and the flask is lightly shaken to obtain a suspension of liposomes. The suspension of liposomes is entered into a centrifugal tube and cooled to 10° C. and then centrifuged at 27,000 G for 20 minutes, by which creamy liposomes are obtained at the upper part. The transparent aqueous layer is again treated with lecithin and the mixture is treated in the flask in the same manner as above. The procedure is repeated three times. The creamy liposomes obtained in the above three times procedures are combined and suspended in physiological saline (50 ml) and thereto is added an appropriate amount of distilled water and the liposomes are uniformly dispersed therein. The mixture is rapidly frozen by cooling at −40° C. to −60° C. and lyophilized under reduced pressure with sublimating water. (During the lyophilization, sugars may be added to the liposome particles as a stabilizer)

The lyophilized liposome product thus obtained contains coagulation factor VIII of 1,000 units and aprotinin of 50,000 units. The lyophilized liposome product is lightly pulverized under dry nitrogen stream and then is packed in intestine capsules (size: #0). After the joint of the capsules is completely sealed by treating them with a solution of intestine capsule-forming material in acetone, the capsules are air-dried. The intestine capsules thus obtained contains coagulation factor VIII of 50 units per each capsule. This product can be kept for a long period of time when kept at a cool and dark place. The liposomes in this product can easily be restored into the original form by adding water thereto.

EXAMPLE 3

Coagulation factor VIII (2,000 units), yolk lecithin (5 g) containing 15% of phosphatidic acid, and an injection liquid of aprotinin (50 thousand units) are each lyophilized, wherein the factor VIII is lyophilized as it stands, the lecithin is lyophilized in the form of a solution in benzene, and the aprotinin injection liquid is lyophilized as it stands. The lyophilized powders are mixed under dry nitrogen stream, and the mixture is packed in intestine capsules (size: #0). (In order to improve fluidity of the mixture, an appropriate amount of sugars such as glucose, lactose or mannitol may be added thereto). The joint of capsules is sealed by treating them with a solution of intestine capsule-forming material in acetone like in Examples 1 and 2. The intestine capsules contain coagulation factor VIII of 100 units per each capsule. This product is very stable and can be kept for a long period of time. The liposomes in this product can easily be restored into the original form by adding a small amount of water thereto, and a fairly amount of the factor VIII is enclosed in the liposomes.

EXAMPLE 4

Yolk lecithin (2 g) containing 5% of phosphatidic acid is dissolved in ethanol (40 ml) and the solution is concentrated under reduced pressure in a one-liter flask to deposit the lecithin as a thin layer on the inner wall of the flask. After drying under reduced pressure, a phosphate buffer solution (pH 7.0, 50 ml) containing coagulation factor VIII (3,000 units) and aprotinin (50 thousand units) is added thereto, and the flask is lightly shaken to obtain a suspension of liposomes. The suspension of liposomes is treated in the same manner as described in Example 1 to give liposomes of about 10 ml, which contain coagulation factor VIII of 1,000 units and aprotinin of 17,000 units. The liposomes thus obtained are packed in intestine capsules like in Example 1. The capsules thus obtained contain the factor VIII of 50 units per each capsule. This product can be kept without lowering of the activity of the factor VIII by keeping it at a cool and dark place.

REFERENCE EXAMPLE 1

Yolk lecithin (250 mg) containing 5% of phosphatidic acid is dissolved in ethanol (40 ml) and the solution is concentrated under reduced pressure in a 200 ml flask to deposit the lecithin as a thin layer on the inner wall of flask. After drying under reduced pressure, an aqueous solution of coagulation factor VIII (4,000 units) is added thereto, and the mixture is lightly shaken to obtain a suspension of liposomes. The suspension of liposomes is entered into a centrifugal tube and cooled to 10° C. and then is centrifuged at 27,000 G for 20 minutes, by which creamy liposomes are obtained at the upper part. The transparent aqueous layer is again treated with lecithin and the mixture is treated in the flask in the same manner as above. This procedure is repeated twice. The creamy liposomes obtained in the above twice procedures are combined and suspended in physiological saline (50 ml), by which the outer layer of liposomes is washed. Under cooling at 10° C., the mixture is centrifuged at 50,000 G for 20 minutes to collect liposomes. The liposomes are diluted with physiological saline so as to become totally 50 ml. The suspension thus obtained (50 ml) contains coagulation factor VIII of 800 units.

REFERENCE EXAMPLE 2

Yolk lecithin (2 g) containing 5% of phosphatidic acid is dissolved in ethanol (40 ml) and the solution is concentrated under reduced pressure in a one-liter flask to deposit the lecithin as a thin layer on the inner wall of the flask. After drying under reduced pressure, a phosphate buffer solution (pH 7.0, 50 ml) containing coagulation factor VIII (3,000 units) is added thereto, and the mixture is lightly shaken to obtain a suspension of liposomes. The suspension of liposomes is treated in the same manner as described in Example 1 to give liposomes of 10 ml. The liposomes are packed in gelatine capsules. This product contains coagulation factor VIII of 50 units per each capsule.

REFERENCE EXAMPLE 3

The liposomes (10 ml) containing coagulation factor VIII obtained in the same manner as in Reference Example 2 are packed in gelatine capsules (size: #0, inner wall being coated with a thin layer of edible oil), which are further packed in intestine capsules so as to become double capsule structure. The joint of the outer capsules is completely sealed by treating them with a solution of the intestine capsule-forming material in acetone. The capsules contain coagulation factor VIII of 50 units per each capsule.

EXAMPLE 5

Yolk lecithin (1 g) containing 10% of phosphatidic acid is dissolved in ethanol (20 ml) and the solution is concentrated under reduced pressure in a one-liter flask to deposit the licithin as a thin layer on the inner wall of the flask. After drying under reduced pressure, a phosphate buffer solution (pH 7.0, 20 ml) containing $Ca^{++}$ ion and coagulation factor IX (400 units) and aprotinin (50 thousand units), and the flask is lightly shaken to obtain a suspension of liposomes. The suspension of liposomes is entered into a centrifugal tube and cooled to 10° C. and then centrifuged at 27,000 G for 20 minutes, by which creamy liposomes are obtained at the upper part. The transparent aqueous layer is again treated with lecithin and the mixture is treated in the flask in the same manner as above. This product is repeated three times. The creamy liposomes obtained in the above three times procedures are combined and suspended in physiological saline (20 ml), by which the outer layer of liposomes is washed. Under cooling at 10° C., the suspension is centrifuged at 40,000 G for 10 minutes to collect liposomes, and the liposomes are dried in order to remove water contained in the outer layer thereof as largely as possible. The liposomes thus obtained have a volume of about 10 ml and contain coagulation factor IX of 200 units and aprotinin of 15,000 units.

The liposomes obtained above are packed in gelatine capsules (size: #0, inner wall being coated with a thin layer of edible oil), which are further packed in intestine capsules so as to become double capsule structure. The joint of the outer capsules is completely sealed by treating them with a solution of the intestine capsule-forming material in acetone. The capsules contain coagulation factor IX of 40 units per each capsule. When the capsules are kept at a cool and dark place, activity of the factor IX does not lower within a short period of time.

EXAMPLE 6

In the same manner as described in Example 5, yolk lecithin (1 g) containing 10% of phosphatidic acid or calcium phosphatidate is dissolved in ethanol (20 ml), and the solution is concentrated under reduced pressure in a one-liter flask to deposit the lecithin as a thin layer on the inner wall of the flask. After drying under reduced pressure, a phosphate buffer solution (pH 7.0) containing calcium ion and coagulation factor IX (400 units) and aprotinin (50 thousand units), and the flask is lightly shaken to obtain a suspension of liposomes. The suspension of liposomes is entered into a centrifugal tube and cooled to 10° C. and then centrifuged at 27,000 G for 20 minutes, by which creamy liposomes are obtained at the upper part. The aqueous layer is again treated with lecithin and the mixture is treated in the flask in the same manner as above. The procedure is repeated three times. The creamy liposomes obtained in the above three times procedures are combined and suspended in physiological saline (30 ml) and thereto is further added an appropriate amount of distilled water, and the liposomes are uniformly dispersed therein. The mixture is rapidly frozen by cooling at −40° to −60° C. and lyophilized under reduced pressure with sublimating water. (During the lyophilization, stabilizers such as sugars may be added to the liposome particles)

The lyophilized liposome product thus obtained contains coagulation factor IX of 200 units and aprotinin of 15,000 units. The lyophilized liposome product is lightly pulverized under dry nitrogen stream and then is packed in intestine capsules (size: #0). After the joint of the capsules is completely sealed by treating them with a solution of intestine capsule-forming material in acetone, and the capsules are air-dried. The intestine capsules thus obtained contain coagulation factor IX of 50 units per each capsule. This product can be kept for a long period of time when kept at a cool and dark place. The liposomes in this product can easily be restored into the original form by adding water thereto.

EXAMPLE 7

Coagulation factor IX (400 units), yolk lecithin (1 g) containing 10% of calcium phosphatidate, and a phosphate buffer solution (pH 7.0) containing calcium ion and aprotinin (50 thousand units) are each lyophilized, wherein the factor IX is lyophilized as it stands, the lecithin is lyophilized in the form of a solution in benzene, and the aprotinin-containing solution is lyophilized as it stands. The three lyophilized powders thus obtained are mixed under dry nitrogen stream and the mixture is packed in intestine capsules (size: #0). (In order to improve the fluidity of the mixture, an appropriate amount of sugars such as glucose, lactose or mannitol may be added thereto) The joint of the capsules is sealed by treating them with a solution of capsule-forming material in acetone like in Examples 1 and 2. The capsules contain coagulation factor IX of 50 units or more per each capsule. This product is very stable and can be kept for a long period of time. The liposomes in this product can easily be restored into the original form by adding water thereto, and a fairly amount of the factor IX is enclosed in the liposomes.

EXAMPLE 8

Yolk lecithin (1 g) containing 5% of phosphatidic acid is dissolved in ethanol (20 ml), and the solution is concentrated under reduced pressure in a one-liter flask to deposit the lecithin as a thin layer on the inner wall of the flask. After drying under reduced pressure, a phosphate buffer solution (pH 7.0, 20 ml) containing coagulation factor IX (400 units) and aprotin (50 thousand units) is added thereto, and the flask is lightly shaken to give a suspension of liposomes. The suspension of liposomes thus obtained is treated in the same manner as described in Example 5 to give liposomes of 10 ml. This product contains coagulation factor IX of 130 units and aprotinin of 15,000 units.

What is claimed is:

1. A pharmaceutical composition for oral administration, which comprises effective amounts of coagulation factor VIII or IX and a protease inhibitor which are incorporated in liposomes.

2. A composition according to claim 1, wherein the composition is encapsulated in intestine capsules.

3. A composition according to claim 1, wherein the composition is in the form of a lyophilized product.

4. A composition according to claim 3, wherein the composition is encapsulated in intestine capsules.

5. A composition according to claim 1, wherein the coagulation factor is coagulation factor VIII.

6. A composition according to claim 5, wherein the composition is encapsulated in intestine capsules.

7. A composition according to claim 1, wherein the coagulation factor is coagulation factor IX.

8. A pharmaceutical composition for oral administration, which comprises effective amounts of coagulation factor VIII or IX, a protease inhibitor, and liposome-forming material, which are each separately lyophilized.

9. A composition according to claim 8, wherein the lyophilized products are encapsulated in intestine capsules.

10. A pharmaceutical composition for oral administration in the form encapsulated in intestine capsules, which comprises effective amounts of coagulation factor VIII or IX and aprotinin which are incorporated in liposomes formed from a mixture of a phospholipid and phosphatidic acid.

11. A composition according to claim 10, wherein the coagulation factor is coagulation factor VIII.

12. A composition according to claim 10, wherein the coagulation is coagulation factor IX.

13. A lyophilized pharmaceutical composition for oral administration in the form encapsulated in intestine capsules, which comprises effective amounts of coagulation factor VIII and aprotinin which are incorporated in liposomes formed from a mixture of a phospholipid and phosphatidic acid.

14. A method for the treatment and prophylaxis of hemophilia A or B, which comprises administering orally a composition comprising effective amounts of coagulation factor VIII or IX and a protease inhibitor which are incorporated in liposomes to a patient who are deficient in coagulation factor VIII or IX.

* * * * *